(12) United States Patent
Kanai et al.

(10) Patent No.: US 11,840,738 B2
(45) Date of Patent: Dec. 12, 2023

(54) METHOD FOR DETERMINING RISK OF UROTHELIAL CARCINOMA

(71) Applicant: KEIO UNIVERSITY, Minato-ku (JP)

(72) Inventors: Yae Kanai, Shinjuku-ku (JP); Eri Arai, Shinjuku-ku (JP)

(73) Assignee: KEIO UNIVERSITY, Minato-ku (JP)

( * ) Notice: Subject to any disclaimer, the term of this patent is extended or adjusted under 35 U.S.C. 154(b) by 0 days.

(21) Appl. No.: 16/970,583

(22) PCT Filed: Mar. 19, 2019

(86) PCT No.: PCT/JP2019/011442
§ 371 (c)(1),
(2) Date: Aug. 17, 2020

(87) PCT Pub. No.: WO2019/181941
PCT Pub. Date: Sep. 26, 2019

(65) Prior Publication Data
US 2021/0404009 A1    Dec. 30, 2021

(30) Foreign Application Priority Data

Mar. 19, 2018  (JP) ................. 2018-051464

(51) Int. Cl.
*C12Q 1/6886*    (2018.01)

(52) U.S. Cl.
CPC ..... *C12Q 1/6886* (2013.01); *C12Q 2600/154* (2013.01)

(58) Field of Classification Search
CPC .................... C12Q 1/6886; C12Q 2600/154
See application file for complete search history.

(56) References Cited

U.S. PATENT DOCUMENTS

| 2016/0138097 A1 | 5/2016 | Yotani et al. |
| 2017/0058355 A1 | 3/2017 | Kanai et al. |
| 2019/0360049 A1 | 11/2019 | Kanai et al. |

FOREIGN PATENT DOCUMENTS

| EP | 3 048 176 A2 | 7/2016 |
| JP | 2010-207162 A | 9/2010 |
| WO | WO 2013/168644 A1 | 11/2013 |
| WO | WO 2015/129916 A1 | 9/2015 |
| WO | WO 2016/044142 A1 | 3/2016 |
| WO | WO 2017/038983 A1 | 9/2017 |

OTHER PUBLICATIONS

Kandimalla (European Urology, 2012, vol. 6, pp. 1245-1256).*
Tommasi et al. Breast Cancer Research, 2009, 11:R14, pp. 1-17.*
Feber et al. Clinical Epigenetics, 2017, 9:8, pp. 1-10.*
Tsumura, K. et al., "Carcinogenic risk estimation based on genome-wide DNA methylation analysis during urothelial carcinogenesis", Cancer Science, Jan. 2018, vol. 109, Supp 1., p. 49, (J-1003)(Meeting info: 76th Annual Meeting of the Japanese Cancer Association; Sep. 28-30, 2017; Yokohama, Japan), total pages: 2.
Arai, E. "(4) Molecular Pathology of Kidney and Urinary Tract Tumors", The Official Journal of Japanese Society of Laboratory Medicine, 2017, vol. 65, No. 9, pp. 1018-1027.
Kanai, Y., "Epigenetic mechanism of urothelial carcinogenesis: Significance of DNA methylation abnormality in temporal and spatial multiple," Pathology and Clinical Medicine, Sep. 1, 2017, vol. 35, No. 9, pp. 852-857.
Tsumura, K. et al., "Comprehensive DNA methylation analysis during urothelial carcinogenesis", Proceedings of the Japanese Society of Pathology, Apr. 12, 2016, vol. 105, No. 1, p. 433 (P1-253), total pages: 3.
López, J., et al., "A DNA Hypermethylation Profile Reveals New Potential Biomarkers for the Evaluation of Prognosis in Urothelial Bladder Cancer", APMIS. Sep. 2017; 125(9):787-796.
Chihara, Y. et al., "Diagnostic markers of urothelial cancer based on DNA methylation analysis", BMC Cancer, vol. 13, Article No. 275 (2013), pp. 1-10 (total pages: 12).
Issa, J-P. "PERSEPECTIVES: CpG island methylator phenotype in cancer," Nature Reviews, vol. 4, Dec. 2004, pp. 988-993.
Toyota, M. et al. "CpG island methylator phenotype in colorectal cancer," Proc. Natl. Acad. Sci. USA, vol. 96, 1999, pp. 8681-8686.
Shen, L. et al., "Integrated genetic and epigenetic analysis identifies three different subclasses of colon cancer," Proc. Natl. Acad. Sci. USA, vol. 104, No. 47, Nov. 20, 2007, pp. 18654-18659 (total pages: 17).
Toyota, M. et al., "Aberrant Methylation in Gastric Cancer Associated with the CpG Island Methylator Phenotype[1]," Cancer Research, vol. 59, Nov. 1, 1999, pp. 5438-5442.
Nishiyama, N. et al., "Genome-wide DNS methylation profiles in urothelial carcinomas and urothelial at the precancerous stage," Cancer Science, vol. 101, No. 1, Jan. 2010, pp. 231-240.
Verma. M., "Cancer Epigenetics: Risk Assessment, Diagnosis, Treatment, and Prognosis," Methods in Molecular Biology, vol. 1238, 2015, pp. 183-215 (total pages: 37).
International Search Report dated May 14, 2019 in PCT/JP2019/011442 filed on Mar. 19, 2019, 2 pages.
Extended European Search Report dated Sep. 2, 2022, (client received EESR on Sep. 29, 2022) in corresponding European Patent Application No. 19772520.3, 7 pages.

(Continued)

*Primary Examiner* — Sarae L Bausch
(74) *Attorney, Agent, or Firm* — Oblon, McClelland, Maier & Neustadt, L.L.P.

(57) ABSTRACT

A method for determining a risk of urothelial carcinoma may be based on the methylation level of DNA. A method for determining a risk of canceration of a urothelial tissue may involve detecting the DNA methylation level of a CpG site of at least one gene selected from TENM3, HOXC4, TLR1, CPVL and PRDM16 in genomic DNA preferably derived from a urothelial cell or a tissue containing the urothelial cell; and determining a risk of canceration of the urothelial tissue from the detected DNA methylation level.

7 Claims, 3 Drawing Sheets

Specification includes a Sequence Listing.

(56) References Cited

OTHER PUBLICATIONS

Anonymous: "Infinium HumanMethylation450 BeadChip", Mar. 9, 2012, XP55401052A, Retrieved from the Internet: URL:https://support.illumina.com/content/dam/illuminamarketing/documents/products/datasheets/datasheet_humanmethylation450/pdf [retrieved on Aug. 24, 2017], 4 pages.

* cited by examiner

METHOD FOR DETERMINING RISK OF UROTHELIAL CARCINOMA

SEQUENCE LISTING

The instant application contains a Sequence Listing which has been submitted electronically in ASCII format and is hereby incorporated by reference in its entirety. Said ASCII copy, created on Aug. 27, 2021, is named 531987US-ST25.txt and is 3,349 bytes in size.

TECHNICAL OF THE INVENTION

The present invention relates to a method for determining the risk of urothelial carcinoma.

BACKGROUND OF THE INVENTION

Urothelial carcinoma is clinicopathologically characterized by multiple temporal and spatial occurrences, that is, synchronous and metachronous occurrences of lesions in multiple or extensive areas of the renal pelvis, ureter and bladder. A notable example of multiple spatial occurrences includes high-grade flat intraepithelial carcinoma that spreads widely to the entire urinary tract from the renal pelvis to the urethra. High-grade flat intraepithelial carcinoma is a precursor lesion of nonpapillary (nodular) invasive urothelial carcinoma, which is highly malignant and has a poor prognosis. By contrast, low-grade superficial papillary urothelial carcinoma has frequent recurrence (metachronous multiple occurrences), but has a favorable prognosis. However, the low-grade papillary urothelial carcinoma may exhibit a higher grade after repeated recurrences, and may progress to high-grade papillary urothelial carcinoma, then to nonpapillary (nodular) invasive urothelial carcinoma.

Transurethral resection (TUR) or conservative therapy by BCG injection is first selected as a treatment method for urothelial carcinoma, since lesions in the urinary tract can be observed using a cystoscope, and a cytological diagnosis can be repeatedly performed non-invasively, and more importantly, total cystectomy significantly limits QOL. On the other hand, because urothelial carcinoma has multiple occurrences, it is not easy to determine the final consultation even if the surgical treatment seems to have succeeded, and a long-term careful follow-up is needed. Physicians are required to make appropriate judgments regarding the timing of application of surgical treatment and the surgical methods in order to better maintain the patient's QOL and life prognosis.

In recent years, it has become clear that abnormal methylation of DNA is deeply involved in canceration, and has been attracting attention. Abnormal DNA methylation of CpG islands in some gene promoter regions is known as a characteristic epigenetic abnormality in cancer cells. A CpG island is a region in which a two-nucleotide sequence of cytosine (C)-guanine (G) via a phosphodiester bond (p) frequently appears, and is often located in the promoter region upstream of a gene. Abnormal DNA methylation of CpG islands is involved in carcinogenesis through inactivation of tumor suppressor genes and the like. In colorectal carcinoma, gastric carcinoma, renal cell carcinoma, and the like, increased DNA methylation of CpG islands correlating with clinicopathological factors has been reported (Non Patent Literatures 1 to 4, Patent Literatures 1 to 4). Regarding urothelial carcinoma, prediction of the risk of developing urothelial carcinoma by measuring the DNA methylation rate of clinical samples has been reported (Non Patent Literature 5). Furthermore, it has been reported that non-cancerous urothelium obtained from a case of urothelial carcinoma exhibits a DNA methylation profile different from that of normal urothelium, which suggests that abnormal DNA methylation contributes to the multiple temporal and spatial occurrences of urothelial carcinoma (Non Patent Literature 6). Moreover, although not necessarily focused on the multiple temporal and spatial occurrences of urothelial carcinoma, the increased DNA methylation in the homeotic gene HOX gene group, TBX2 and GATA2 which encode transcription factors, receptor tyrosine kinase FGFR3, and histone methyltransferase EZH2, and the reduced DNA methylation in the repetitive sequence LINE-1 have been reported to be associated with urothelial carcinoma (Non Patent Literature 7).

As a method for analyzing methylated DNA, a method utilizing a bisulfite method has already been established and is widely used. The Methylation-Specific PCR (MSP) method, Combined Bisulfite Restriction Analysis (COBRA) method, and BAC array-based methylated CpG island amplification method (BAMCA method) are often used as methylated DNA analysis methods based upon the bisulfite method. Patent Literature 1 discloses a method for detecting the risk of developing urothelial carcinoma, the risk of poor prognosis, and the like by detecting the methylation level of the CpG sites of a specific gene by BAMCA method. However, in this method, the average level of DNA methylation rate of a large number of CpG sites on the BAC clone is measured by hybridization of the entire BAC, which makes the CpG sites with a high diagnostic accuracy unclear, and makes the measurement method cumbersome and difficult to implement in a medical treatment. Patent Literature 2 discloses a method for detecting the risk of poor prognosis for renal cell carcinoma by detecting the methylation level of the CpG sites of a specific gene by a bead array method, mass spectrometry (MassARRAY method), pyrosequencing, methylation-sensitive high resolution melting curve analysis, quantitative PCR, direct sequencing of bisulfite-treated products, COBRA method and the like. Patent Literatures 3 and 4 disclose methods for determining the prognosis of carcinoma by detecting the methylation level of the CpG sites of a specific gene based on the difference in retention time by ion exchange chromatography.

CITATION LIST

Patent Literature

Patent Literature 1: JP-A-2010-207162
Patent Literature 2: WO 2013/168644
Patent Literature 3: WO 2015/129916
Patent Literature 4: WO 2017/038983

Non Patent Literature

Non Patent Literature 1: Nat. Rev. Cancer, 4, 988-993 (2004)
Non Patent Literature 2: Proc. Natl. Acad. Sci. USA, 96, 8681-8686 (1999)
Non Patent Literature 3: Proc. Natl. Acad. Sci. USA, 104, 18654-18659 (2007)
Non Patent Literature 4: Cancer Res., 59, 5438-5442 (1999)
Non Patent Literature 5: Cancer Sci., 101 (1), 231-240 (2010)

Non Patent Literature 6: Pathology and Clinical Medicine, 35 (9), 852-857 (2017)

Non Patent Literature 7: Methods Mol. Biol., 1238, 183-215 (2015)

SUMMARY OF THE INVENTION

Problem to be Solved by the Invention

The present invention provides a method for determining the risk of urothelial carcinoma based on the methylation level of DNA.

Means for Solving the Invention

The present inventors have identified genes that are more highly methylated in urothelial tissues of patients with urothelial carcinoma than in normal tissues. Furthermore, the present inventors have found that the risk of developing urothelial carcinoma can be determined by measuring the DNA methylation level of these genes.

Therefore, the present invention provides the following.

[1] A method for determining a risk of canceration of a urothelial tissue, comprising:
  detecting a DNA methylation level of a CpG site of at least one gene selected from the group consisting of TENM3, HOXC4, TLR1, CPVL and PRDM16 in genomic DNA derived from a urothelial cell or a tissue containing the urothelial cell; and
  determining a risk of canceration of the urothelial tissue from the detected DNA methylation level.

[2] The method according to [1], wherein the detection of the DNA methylation level comprises detecting the DNA methylation level of the CpG site of the at least one gene using the genomic DNA treated with bisulfite.

[3] The method according to [2], wherein the detection of the DNA methylation level is performed using a pyrosequencing method, mass spectrometry, a bead array method or ion exchange chromatography.

[4] The method according to any one of [1] to [3], wherein
  the CpG site of the TENM3 is at least one CpG site selected from the group consisting of CpG sites contained in a polynucleotide consisting of the nucleotide sequence set forth in SEQ ID NO: 1 or a nucleotide sequence having at least 95% identity with the sequence;
  the CpG site of the HOXC4 is at least one CpG site selected from the group consisting of CpG sites contained in a polynucleotide consisting of the nucleotide sequence set forth in SEQ ID NO: 2 or a nucleotide sequence having at least 95% identity with the sequence;
  the CpG site of the TLR1 is at least one CpG site selected from the group consisting of CpG sites contained in a polynucleotide consisting of the nucleotide sequence set forth in SEQ ID NO: 3 or a nucleotide sequence having at least 95% identity with the sequence;
  the CpG site of the CPVL is at least one CpG site selected from the group consisting of CpG sites contained in a polynucleotide consisting of the nucleotide sequence set forth in SEQ ID NO: 4 or a nucleotide sequence having at least 95% identity with the sequence; and
  the CpG site of the PRDM16 is at least one CpG site selected from the group consisting of CpG sites contained in a polynucleotide consisting of the nucleotide sequence set forth in SEQ ID NO: 5 or a nucleotide sequence having at least 95% identity with the sequence.

[5] The method according to any one of [1] to [3], wherein, based on the NCBI database Genome Build 37,
  the CpG site of the TENM3 is located at at least one position selected from the group consisting of position 183,710,473, position 183,710,455, position 183,710,441, position 183,710,349, position 183,710,344, position 183,710,318, and position 183,710,311 of chromosome 4;
  the CpG site of the HOXC4 is located at at least one position selected from the group consisting of position 54,438,419 and position 54,438,426 of chromosome 12;
  the CpG site of the TLR1 is located at position 38,807,259 of chromosome 4;
  the CpG site of the CPVL is located at position 29,187,019 of chromosome 7; and
  the CpG site of the PRDM16 is located at position 3,078,013 of chromosome 1.

[6] A primer or probe for determining a risk of urothelial carcinoma, which has a length of at least 12 bases, and is hybridized to a CpG site contained in at least one gene selected from the group consisting of TENM3, HOXC4, TLR1, CPVL and PRDM16 that have been treated with bisulfite.

[7] The primer or probe according to [6], wherein
  the CpG site of the TENM3 is at least one CpG site selected from the group consisting of CpG sites contained in a polynucleotide consisting of the nucleotide sequence set forth in SEQ ID NO: 1 or a nucleotide sequence having at least 95% identity with the sequence;
  the CpG site of the HOXC4 is at least one CpG site selected from the group consisting of CpG sites contained in a polynucleotide consisting of the nucleotide sequence set forth in SEQ ID NO: 2 or a nucleotide sequence having at least 95% identity with the sequence;
  the CpG site of the TLR1 is at least one CpG site selected from the group consisting of CpG sites contained in a polynucleotide consisting of the nucleotide sequence set forth in SEQ ID NO: 3 or a nucleotide sequence having at least 95% identity with the sequence;
  the CpG site of the CPVL is at least one CpG site selected from the group consisting of CpG sites contained in a polynucleotide consisting of the nucleotide sequence set forth in SEQ ID NO: 4 or a nucleotide sequence having at least 95% identity with the sequence; and
  the CpG site of the PRDM16 is at least one CpG site selected from the group consisting of CpG sites contained in a polynucleotide consisting of the nucleotide sequence set forth in SEQ ID NO: 5 or a nucleotide sequence having at least 95% identity with the sequence.

[8] The primer or probe according to [6], wherein, based on the NCBI database Genome Build 37,
  the CpG site of the TENM3 is located at at least one position selected from the group consisting of position 183,710,473, position 183,710,455, position 183,710,441, position 183,710,349, position 183,710,344, position 183,710,318, and position 183,710,311 of chromosome 4;

the CpG site of the HOXC4 is located at at least one position selected from the group consisting of position 54,438,419 and position 54,438,426 of chromosome 12;

the CpG site of the TLR1 is located at position 38,807,259 of chromosome 4;

the CpG site of the CPVL is located at position 29,187,019 of chromosome 7; and the CpG site of the PRDM16 is located at position 3,078,013 of chromosome 1.

[9] The primer or probe according to any one of [6] to [8], which is selected from the group consisting of polynucleotides consisting of the nucleotide sequences set forth in SEQ ID NOs: 6 to 15 and the complementary strands thereof.

[10] The primer or probe according to [9], which is a primer set consisting of a combination of the polynucleotides set forth in SEQ ID NOs: 6 and 7, the polynucleotides set forth in SEQ ID NOs: 8 and 9, the polynucleotides set forth in SEQ ID NOs: 10 and 11, the polynucleotides set forth in SEQ ID NOs: 12 and 13, the polynucleotides set forth in SEQ ID NOs: 14 and 15, or the complementary strands thereof.

[11] A method for determining a risk of urothelium carcinoma in a subject, comprising:

detecting a DNA methylation level of a CpG site of at least one gene selected from the group consisting of TENM3, HOXC4, TLR1, CPVL and PRDM16 in genomic DNA derived from a urothelial cell or a tissue containing the urothelial cell in the subject; and determining a risk of urothelium carcinoma in the subject from the detected DNA methylation level.

[12] The method according to [11], wherein the detection of the DNA methylation level comprises detecting the DNA methylation level of the CpG site of the at least one gene using the genomic DNA treated with bisulfite.

[13] The method according to [12], wherein the detection of the DNA methylation level is performed using a pyrosequencing method, mass spectrometry, a bead array method or ion exchange chromatography.

[14] The method according to any one of [11] to [13], wherein the CpG site of the TENM3 is at least one CpG site selected from the group consisting of CpG sites contained in a polynucleotide consisting of the nucleotide sequence set forth in SEQ ID NO: 1 or a nucleotide sequence having at least 95% identity with the sequence;

the CpG site of the HOXC4 is at least one CpG site selected from the group consisting of CpG sites contained in a polynucleotide consisting of the nucleotide sequence set forth in SEQ ID NO: 2 or a nucleotide sequence having at least 95% identity with the sequence;

the CpG site of the TLR1 is at least one CpG site selected from the group consisting of CpG sites contained in a polynucleotide consisting of the nucleotide sequence set forth in SEQ ID NO: 3 or a nucleotide sequence having at least 95% identity with the sequence;

the CpG site of the CPVL is at least one CpG site selected from the group consisting of CpG sites contained in a polynucleotide consisting of the nucleotide sequence set forth in SEQ ID NO: 4 or a nucleotide sequence having at least 95% identity with the sequence; and the CpG site of the PRDM16 is at least one CpG site selected from the group consisting of CpG sites contained in a polynucleotide consisting of the nucleotide sequence set forth in SEQ ID NO: 5 or a nucleotide sequence having at least 95% identity with the sequence.

[15] The method according to any one of [11] to [13], wherein, based on the NCBI database Genome Build 37, the CpG site of the TENM3 is located at at least one position selected from the group consisting of position 183,710,473, position 183,710,455, position 183,710,441, position 183,710,349, position 183,710,344, position 183,710,318, and position 183,710,311 of chromosome 4;

the CpG site of the HOXC4 is located at at least one position selected from the group consisting of position 54,438,419 and position 54,438,426 of chromosome 12;

the CpG site of the TLR1 is located at position 38,807,259 of chromosome 4;

the CpG site of the CPVL is located at position 29,187,019 of chromosome 7; and the CpG site of the PRDM16 is located at position 3,078,013 of chromosome 1.

Effects of the Invention

According to the present invention, the risk of urothelial carcinoma can be determined easily and with high sensitivity and specificity. The present invention provides a guideline for preventive intervention such as lifestyle improvement for preventing the development of future urothelial carcinoma in a medical check examinee or the like, enables early diagnosis when the carcinoma has actually developed, and contributes to the improvement of the patient's QOL and survival rate.

EMBODIMENTS FOR CARRYING OUT THE INVENTION

Figure 1:
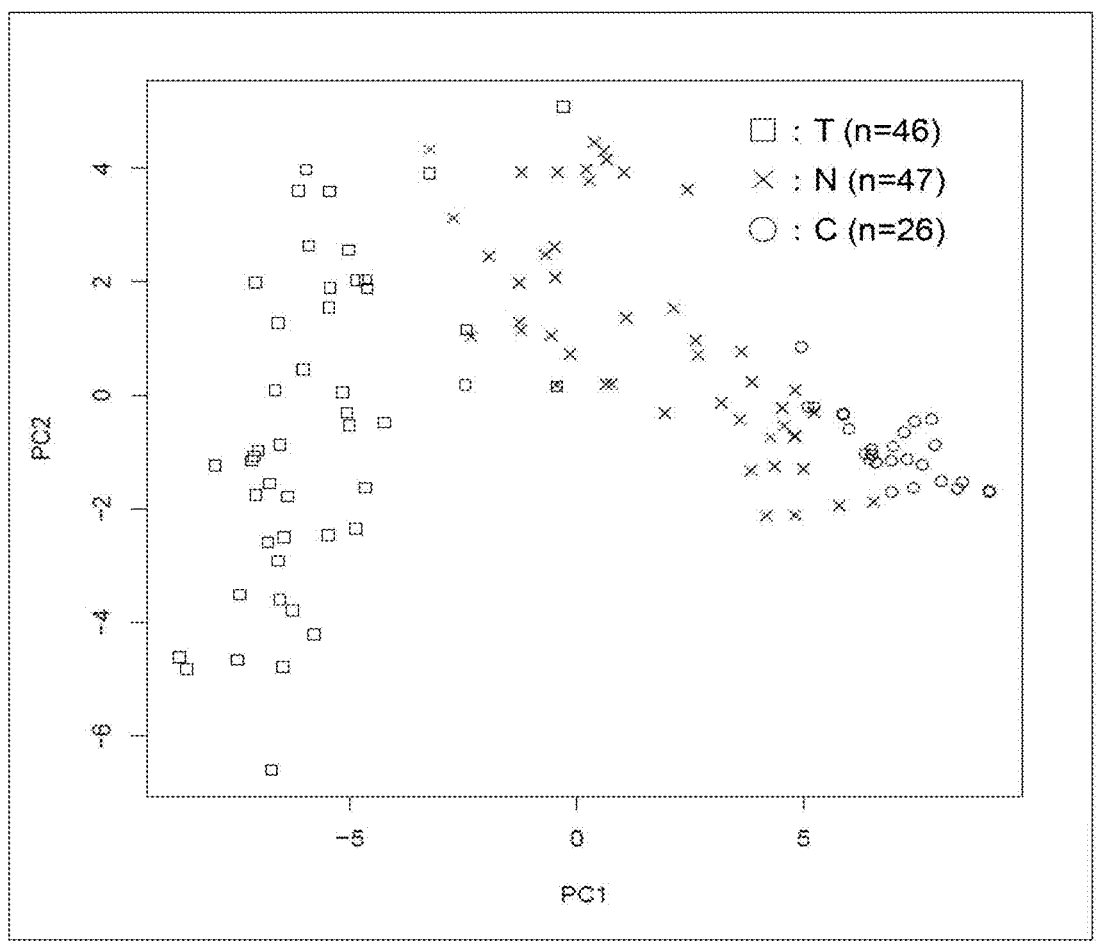
FIG. 1 Principal component analysis using the 2,750 probes in the Infinium (registered trademark) assay to analyze changes in DNA methylation levels. (C): Specimens derived from normal tissues (n=26), (N): Specimens derived from non-cancerous tissues of patients with urothelial carcinoma (n=47), (T): Specimens derived from urothelial carcinoma tissues (n=46).

In the present description, "urothelial carcinoma" refers to a carcinoma that occurs in the epithelial cells of the urinary tract including the renal pelvis, ureter, and urethra. Since urothelial carcinoma has multiple metachronous or synchronous occurrences, "urothelial carcinoma" in the present description includes primary carcinoma and carcinoma that has metastasized within a tissue. In addition, in the present description, examples of the "subject" include a human, e.g., a person who is in need of determination of the risk of urothelial carcinoma (for example, a medical check examinee), and a patient suspected of having urothelial carcinoma.

In the present description, the "risk of carcinoma" refers to the risk of having carcinoma or the risk of developing carcinoma in the future. In the present description, the "risk of tissue canceration" refers to the risk that a tissue has carcinoma or the risk that a tissue will have carcinoma in the future. The "tissue" includes a tissue in which carcinoma has not been previously observed, and a tissue suspected of having carcinoma.

In the present description, the "CpG site" means a site where cytosine (C) and guanine (G) are bonded by a phosphodiester bond (p) in DNA. A region where CpG sites appear with high frequency is called a CpG island. CpG islands are often located at a position close to the coding region of a gene, for example, in the promoter region. Therefore, the CpG sites of a gene are predominantly located in the CpG islands located at a position close to the coding region of the gene, or in the promoter region of the gene. In the present description, the "CpG site of a gene", unless otherwise defined, preferably means a CpG site contained in a CpG island located at a position close to the coding region of the gene, and more preferably means a CpG site located in the promoter region of the gene.

In the present description, "DNA methylation" means a state in which the carbon at position 5 of cytosine is methylated in DNA. Moreover, in the present description, the "DNA methylation level" of a CpG site means the proportion of methylated DNA at the CpG site. In the present description, a high or low DNA methylation level means that the proportion of methylated DNA is high or low, respectively.

In the present description, "at least 95% identity" with respect to an amino acid sequence and a nucleotide sequence refers to a 95% or more identity, preferably 96% or more identity, more preferably 97% or more identity, further preferably 98% or more identity, furthermore preferably 99% or more identity.

The present invention provides a method for determining a risk of canceration of a urothelial tissue, comprising:
  detecting a DNA methylation level of a CpG site of at least one gene selected from the group consisting of TENM3, HOXC4, TLR1, CPVL and PRDM16 in genomic DNA derived from a urothelial cell or a tissue containing the urothelial cell in a subject; and
  determining a risk of canceration of the urothelial tissue from the detected DNA methylation level.

In addition, the present invention provides a method for determining a risk of urothelial carcinoma in a subject, comprising:
  detecting a DNA methylation level of a CpG site of at least one gene selected from the group consisting of TENM3, HOXC4, TLR1, CPVL and PRDM16 in genomic DNA derived from a urothelial cell or a tissue containing the urothelial cell in the subject; and
  determining a risk of urothelium carcinoma in the subject from the detected DNA methylation level.

Examples of genomic DNA derived from urothelial cells or tissues containing the same used in the method of the present invention include genomic DNA prepared from urothelial cells or tissues containing the same, and urothelial cell-derived DNA or Cell-Free DNA in urine. Examples of the urothelial cells or tissues containing the same include fresh urothelial tissue collected in surgery or biopsy, frozen urothelial tissue frozen after collection, urothelial tissue that has been fixed in formalin and embedded in paraffin after collection, and urothelial cells concentrated from urine. Among these, frozen urothelial tissue is preferable from the viewpoint of suppressing the degradation of genomic DNA in the tissue and more efficiently detecting the DNA methylation level.

The method for preparing the sample DNA from urothelial tissue or urothelial cells is not particularly limited, and a known method can be appropriately selected and used. Known methods for preparing DNA include the phenol-chloroform method, or a DNA extraction method using a commercially available DNA extraction kit, for example, QIAamp DNA Mini kit (manufactured by Qiagen), Clean Columns (manufactured by NexTec), AquaPure (manufactured by Bio-Rad), ZR Plant/Seed DNA Kit (manufactured by Zymo Research), prepGEM (manufactured by ZyGEM), and BuccalQuick (manufactured by TrimGen), which will be described later. The urothelial cell-derived DNA or cell-free DNA in urine can also be prepared using a commercially available kit for purifying cell-derived DNA or cell-free DNA in urine.

Preferably, the prepared genomic DNA is treated with bisulfite. The method for the bisulfite treatment of DNA is not particularly limited, and a known method can be appropriately selected and used. Examples of known methods for the bisulfite treatment include methods using a commercially available kit such as EpiTect Bisulfite Kit (48) (manufactured by Qiagen), MethylEasy (manufactured by Human Genetics Signatures Pty), Cells-to-CpG Bisulfite Conversion Kit (manufactured by Applied Biosystems), and CpGenome Turbo Bisulfite Modification Kit (manufactured by MERCK MILLIPORE), which will be described later.

Furthermore, it is preferable to amplify the bisulfite-treated DNA. The method of amplification is not particularly limited, but PCR is preferably used. As for the method and conditions of amplification, known methods and conditions can be appropriately selected and used according to the sequence, length, amount, and the like of the DNA to be amplified.

As shown in the Examples described below, the present inventors have made clear that the DNA methylation levels at the CpG sites of five genes (TENM3, HOXC4, TLR1, CPVL and PRDM16) are different between normal urothelial tissue and urothelial tissue derived from patients with urothelial carcinoma. Therefore, the CpG sites that are the target for detecting the DNA methylation level in the method of the present invention are the CpG sites of at least one gene selected from the group consisting of the five genes (that is, TENM3, HOXC4, TLR1, CPVL and PRDM16). Preferably, the CpG sites that are the target for detecting the DNA methylation level in the method of the present invention are the CpG sites of at least one gene selected from the group consisting of TENM3, HOXC4, TLR1, and CPVL.

Therefore, when the DNA treated with bisulfite as described above is amplified by PCR or the like, the region containing the CpG sites of at least one gene selected from the group consisting of the five genes, preferably TENM3, HOXC4, TLR1 and CPVL, is amplified. Preferably, the DNA region containing part or all of the CpG islands or promoter region of at least one gene selected from the group consisting of the five genes, is amplified. More preferably, the DNA region containing part or all of the CpG islands or promoter region of at least one gene selected from the group consisting of TENM3, HOXC4, TLR1 and CPVL, is amplified. Further preferably, the DNA region containing the polynucleotide consisting of the nucleotide sequence set forth in any of SEQ ID NOs: 1 to 5 or a nucleotide sequence having at least 95% identity with the sequence, is amplified. Furthermore preferably, the DNA region containing the polynucleotide consisting of the nucleotide sequence set forth in any of SEQ ID NOs: 1 to 4 or a nucleotide sequence having at least 95% identity with the sequence, is amplified.

TENM3 is a gene encoding the protein identified by RefSeq ID: NP_001073946, HOXC4 is a gene encoding the protein identified by RefSeq ID: NP_705897, TLR1 is a gene encoding the protein identified by RefSeq ID: NP_003254, CPVL is a gene encoding the protein identified by RefSeq ID: NP_001334981, and PRDM16 is a gene encoding the protein identified by RefSeq ID: NP_071397.

Preferably, the CpG site of the TENM3 used in the present invention is at least one CpG site selected from the group consisting of CpG sites contained in a polynucleotide consisting of the nucleotide sequence set forth in SEQ ID NO: 1 or a nucleotide sequence having at least 95% identity with the sequence. Preferably, the CpG site of the TENM3 used in the present invention is a CpG site located at at least one position selected from the group consisting of position 183,710,473, position 183,710,455, position 183,710,441, position 183,710,349, position 183,710,344, position 183,710,318, and position 183,710,311 of chromosome 4.

Preferably, the CpG site of the HOXC4 used in the present invention is at least one CpG site selected from the group consisting of CpG sites contained in a polynucleotide consisting of the nucleotide sequence set forth in SEQ ID NO: 2 or a nucleotide sequence having at least 95% identity with the sequence. Preferably, the CpG sites of the HOXC4 used in the present invention are located at position 54,438,419 and position 54,438,426 of chromosome 12.

Preferably, the CpG site of the TLR1 used in the present invention is at least one CpG site selected from the group consisting of CpG sites contained in a polynucleotide consisting of the nucleotide sequence set forth in SEQ ID NO: 3 or a nucleotide sequence having at least 95% identity with the sequence. Preferably, the CpG site of the TLR1 used in the present invention is located at position 38,807,259 of chromosome 4.

Preferably, the CpG site of the CPVL used in the present invention is at least one CpG site selected from the group consisting of CpG sites contained in a polynucleotide consisting of the nucleotide sequence set forth in SEQ ID NO: 4 or a nucleotide sequence having at least 95% identity with the sequence. Preferably, the CpG site of the CPVL used in the present invention is located at position 29,187,019 of chromosome 7.

Preferably, the CpG site of the PRDM16 used in the present invention is at least one CpG site selected from the group consisting of CpG sites contained in a polynucleotide consisting of the nucleotide sequence set forth in SEQ ID NO: 5 or a nucleotide sequence having at least 95% identity with the sequence. Preferably, the CpG site of the PRDM16 used in the present invention is located at position 3,078,013 of chromosome 1.

In the present description, the position of the CpG site on the chromosome is expressed based on the position on the NCBI database Genome Build 37, which is a human reference genome sequence. The preferable CpG sites used in the present invention are described in Table 1.

TABLE 1

| Gene | Chromosome number | Position on the chromosome | Change in methylation associated with canceration |
|---|---|---|---|
| TENM3 | 4 | 183710473 | Increase |
| | 4 | 183710455 | Increase |
| | 4 | 183710441 | Increase |
| | 4 | 183710349, 183710344 | Increase |
| | 4 | 183710318, 183710311 | Increase |
| HOXC4 | 12 | 54438419 | Reduction |
| | 12 | 54438426 | Reduction |
| TLR1 | 4 | 38807259 | Reduction |
| CPVL | 7 | 29187019 | Reduction |
| PRDM16 | 1 | 3078013 | Reduction |

In the method of the present invention, the CpG site whose DNA methylation level is detected is preferably at least one selected from the group consisting of the CpG sites located at the positions on the chromosome described in Table 1. More preferably, the CpG site whose DNA methylation level is detected in the method of the present invention is at least one selected from the group consisting of the CpG sites located at position 183,710,473, position 183,710,455, position 183,710,441, position 183,710,349, position 183,710,344, position 183,710,318, and position 183,710,311 of chromosome 4 (gene regions of TENM3), position 54,438,419 and position 54,438,426 of chromosome 12 (gene regions of HOXC4), position 38,807,259 of chromosome 4 (gene region of TLR1), and position 29,187,019 of chromosome 7 (gene region of CPVL).

The above-mentioned CpG sites may be used in combination as detection targets from the viewpoint that the sensitivity or specificity of detection of the DNA methylation level can be further improved. Preferable examples of the combination include a combination of any one or more of the CpG sites of TENM3 shown in Table 1 with any one or more of the other CpG sites shown in Table 1, and a combination of any two or more of the CpG sites of TENM3 shown in Table 1. More preferable examples of the combination include at least one selected from the group consisting of combinations of CpG sites shown in Table 2 below.

TABLE 2

| | | CpG site | |
|---|---|---|---|
| Combination No. | Gene | Chromosome number | Position on the chromosome |
| 1 | TENM3 | 4 | 183710473 |
| | HOXC4 | 12 | 54438419 |
| 2 | TENM3 | 4 | 183710473 |
| | HOXC4 | 12 | 54438426 |
| 3 | TENM3 | 4 | 183710473 |
| | TLR1 | 4 | 38807259 |
| 4 | TENM3 | 4 | 183710473 |
| | CPVL | 7 | 29187019 |
| 5 | TENM3 | 4 | 183710455 |
| | HOXC4 | 12 | 54438426 |
| 6 | TENM3 | 4 | 183710349, 183710344 |
| | TLR1 | 4 | 38807259 |
| 7 | TENM3 | 4 | 183710318, 183710311 |
| | HOXC4 | 12 | 54438426 |
| 8 | TENM3 | 4 | 183710318, 183710311 |
| | TLR1 | 4 | 38807259 |
| 9 | HOXC4 | 12 | 54438419 |
| | HOXC4 | 12 | 54438426 |

TABLE 2-continued

| Combination No. | Gene | CpG site Chromosome number | Position on the chromosome |
|---|---|---|---|
| 10 | HOXC4 | 12 | 54438419 |
|  | TLR1 | 4 | 38807259 |
| 11 | HOXC4 | 12 | 54438426 |
|  | TLR1 | 4 | 38807259 |
| 12 | HOXC4 | 12 | 54438426 |
|  | CPVL | 7 | 29187019 |
| 13 | PRDM16 | 1 | 3078013 |
|  | TLR1 | 4 | 38807259 |
| 14 | PRDM16 | 1 | 3078013 |
|  | TENM3 | 4 | 183710473 |
| 15 | PRDM16 | 1 | 3078013 |
|  | TENM3 | 4 | 183710349, 183710344 |
| 16 | PRDM16 | 1 | 3078013 |
|  | TENM3 | 4 | 183710318, 183710311 |
| 17 | PRDM16 | 1 | 3078013 |
|  | HOXC4 | 12 | 54438419 |
| 18 | PRDM16 | 1 | 3078013 |
|  | HOXC4 | 12 | 54438426 |

In the method of the present invention, the technique for detecting the DNA methylation level of a CpG site may be a technique that can quantify the DNA methylation level at a given CpG site, and a known technique can be appropriately selected. Examples of such known techniques include the first to eighth techniques shown below.

The first technique is a method which utilizes a single-base extension reaction using a probe constructed so as to have a base complementary to methylated cytosine or unmethylated cytosine at the 3'-terminus, to quantify the methylation of DNA at a CpG site. For example, the first technique is a method based on the following principles. First, a bisulfite treatment is performed on the genomic DNA. As a result of this bisulfite treatment, unmethylated cytosine residues are converted to uracil, but methylated cytosine residues are not converted (see Clark S J et al., Nucleic Acids Res, 1994, 22, 2990-2997). Next, the whole genome is amplified using the genomic DNA thus treated with bisulfite as a template, enzymatic fragmentation (usually, fragmentation of about 300 to 600 bp) is performed, and the fragments are dissociated into single strands.

In the first technique, a probe, which hybridizes to genomic DNA converted by bisulfite treatment, and in which the base at the 3'-terminus of the probe is a base complementary to the cytosine at the CpG site, is prepared. That is, when the CpG site is methylated, the base at the 3'-terminus of the probe is guanine, and when the CpG site is not methylated, the base at the 3'-terminus of the probe is adenine.

Then, these two types of probe differing only in the base at the 3'-terminus complementary to the CpG site are hybridized with the single-stranded DNA fragment, and a single-base extension reaction is performed in the presence of a fluorescently labeled base. As a result, when the CpG site of the single-stranded fragment is methylated, a fluorescently labeled base is incorporated into the probe in which the 3'-terminal base is guanine (probe for methylation detection) by a single-base extension reaction, but no fluorescently labeled base is incorporated into the probe in which the 3'-terminal base is adenine (probe for unmethylation detection) as no single-base extension reaction occurs due to the mismatch of the 3'-terminal base. On the other hand, when the CpG site of the single-stranded fragment is not methylated, a fluorescently labeled base is incorporated into the probe for unmethylation detection, but no fluorescently labeled base is incorporated into the probe for methylation detection. Therefore, the DNA methylation level can be calculated from the intensity of the fluorescence emitted by the probe for methylation detection and/or the probe for unmethylation detection.

In addition, in this first technique, as another aspect, a probe which hybridizes to genomic DNA converted by bisulfite treatment, and in which the 3'-terminal base of the probe is a base complementary to the guanine at the CpG site, may be used instead of the probe for methylation detection and the probe for unmethylation detection. Then, this probe is hybridized with the single-stranded DNA fragment, and a single-base extension reaction is performed in the presence of guanine labeled with a fluorescent substance and/or adenine labeled with a fluorescent dye different from the fluorescent substance. As a result, when the CpG site is methylated, fluorescently labeled guanine is incorporated into the probe, whereas when the CpG site is not methylated, fluorescently labeled adenine is incorporated into the probe. Therefore, the DNA methylation level can be calculated from the intensity of the fluorescence emitted by each fluorescent substance incorporated into the probe.

A preferable example of this first technique is, for example, a bead array method (for example, Infinium (registered trademark) assay).

The second technique is a method for quantifying methylated DNA by mass spectrometry. For example, the second technique is a method based on the following principles. First, a bisulfite treatment is performed on the genomic DNA. Next, using the bisulfite-treated genomic DNA as a template, the DNA containing at least one of the CpG sites is amplified with a primer to which a T7 promoter is added. Next, the amplified DNA is transcribed into RNA, and a base-specific cleavage reaction is performed with RNase. Then, the product of this cleavage reaction is run through a mass spectrometer to measure the mass.

Then, the mass derived from the methylated cytosine residue (mass of cytosine) obtained by mass measurement is compared to the mass derived from the unmethylated cytosine residue (mass of uracil) to calculate the DNA methylation level at the CpG site.

A preferable example of this second technique is, for example, a DNA methylation analysis method using a mass spectrometer (for example, MassARRAY (registered trademark), see Jurinke C et al., Mutat Res, 2005, 573, 83-95 and Example 2 described below).

In MassARRAY (registered trademark), bisulfite-treated DNA containing the CpG sites is amplified, transcribed into RNA, and then specifically cleaved at the uracil site by RNase. As a result, RNA fragments having different lengths are produced according to the presence or absence of methylation of DNA. The obtained RNA fragments are run through mass spectrometry, which allows to separate and detect the fragments in which the CpG site is methylated from the unmethylated fragments according to the difference in molecular weight. The primer for amplifying the DNA containing the CpG sites can be designed using EpiDesigner (manufactured by SEQUENOM, primer design software for MassARRAY) and the like. For the mass spectrometry of the RNA fragments, MALDI-TOF MS (for example, MassARRAY Analyzer 4 manufactured by SEQUENOM), which can detect the difference in mass of a single base, is used. The methylation level of DNA is calculated from the mass ratio between the RNA fragments derived from methylated DNA and the RNA fragments derived from unmethylated DNA.

The third technique is a method based on the following principles. First, a bisulfite treatment is performed on the genomic DNA. This bisulfite treatment converts the unmethylated cytosine residues to uracil, but uracil is shown as thymine in the following extension reaction (sequence reaction). Next, using the genomic DNA thus treated with bisulfite as a template, the DNA containing at least one of the CpG sites is amplified. Then, the amplified DNA is dissociated into single strands. Next, only one strand of the dissociated single-stranded DNA is separated. Then, an extension reaction is performed one base at a time from the vicinity of the base of the CpG site, the pyrophosphate generated at that time is enzymatically made luminescent, and the intensity of the luminescence is measured. The intensity of the luminescence derived from the methylated cytosine residues thus obtained (luminescence intensity of cytosine) is compared to the intensity of the luminescence derived from the unmethylated cytosine residues (luminescence intensity of thymine), and the DNA methylation level (%) at the CpG site is calculated, for example, by the following expression:

DNA methylation level (%)=luminescence intensity of cytosine×100/(luminescence intensity of cytosine+luminescence intensity of thymine).

Examples of the third technique include the Pyrosequencing method (registered trademark) (see Anal. Biochem. (2000) 10: 103-110).

The fourth technique is a method based on the following principles. First, a bisulfite treatment is performed on the genomic DNA. Next, in a reaction system containing an intercalator which emits fluorescence when inserted between DNA duplexes, the nucleotides containing at least one of the CpG sites are amplified using the bisulfite-treated genomic DNA as a template. Then, the temperature of the reaction system is changed to detect the change in the intensity of the fluorescence emitted by the intercalator. The melting curve of the nucleotides containing at least one of the CpG sites is compared with the melting curve of the amplification product using the methylated/unmethylated control specimen as a template to calculate the DNA methylation level at the CpG site.

An example of the fourth technique is the methylation-sensitive high resolution melting curve analysis (MS-HRM, see Wojdacz T K et al., Nat Protoc., 2008, 3, 1903-1908).

The fifth technique is a method based on the following principles. First, a bisulfite treatment is performed on the genomic DNA. Next, a primer set capable of amplifying when the CpG site is methylated and a primer set capable of amplifying when the CpG site is not methylated are prepared. Then, using the bisulfite-treated genomic DNA as a template, the nucleotides containing at least one of the CpG sites are amplified using each of these primer sets. Then, the DNA methylation level at the CpG site is calculated by comparing the amounts of the obtained amplification products, that is, the amount of methylated CpG site-specific amplification product with the amount of unmethylated CpG site-specific amplification product.

Furthermore, as another aspect of this fifth technique, first, a bisulfite treatment is performed on the genomic DNA. Next, an oligonucleotide probe having nucleotides capable of hybridizing when the CpG site is methylated, and labeled with a fluorescent reporter dye and a fluorescent quencher dye, is prepared. In addition, an oligonucleotide probe having a nucleotide capable of hybridizing when the CpG site is not methylated, and labeled with a fluorescent reporter dye different from the above fluorescent reporter dye and a fluorescent quencher dye, is prepared. Then, the oligonucleotide probe is hybridized to the bisulfite-treated genomic DNA, and the nucleotides containing the CpG site are amplified using the genomic DNA hybridized by the oligonucleotide probe as a template. Then, the fluorescence emitted by the fluorescent reporter dye due to the degradation of the oligonucleotide probe associated with the amplification is detected. The DNA methylation level at the CpG site is calculated by comparing the intensity of the fluorescence emitted by the fluorescent reporter dye specific to the methylated cytosine CpG site thus detected with the intensity of the fluorescence emitted by the fluorescent reporter dye specific to the unmethylated cytosine CpG site.

An example of the fifth technique is the methylation-specific polymerase chain reaction (MS-PCR) using real-time quantitative PCR such as the MethyLight method using a TaqMan probe (registered trademark).

The sixth technique is a method based on the following principles. First, a bisulfite treatment is performed on the genomic DNA. Next, a direct sequencing reaction is performed using the bisulfite-converted nucleotide containing the CpG site as a template. Then, the DNA methylation level at the CpG site is calculated by comparing the fluorescence intensity based on the determined base sequence, that is, the fluorescence intensity derived from the methylated cytosine residues (fluorescence intensity of cytosine) with the fluorescence intensity derived from the unmethylated cytosine residues (fluorescence intensity of thymine).

Furthermore, as another aspect of this sixth technique, first, a bisulfite treatment is performed on the genomic DNA. Next, the bisulfite-converted nucleotides containing the CpG site are cloned by PCR reaction or the like. Then, the base sequences of the obtained cloning products are each determined, and the DNA methylation level at the CpG site is calculated by comparing the number of cloning products having a methylated cytosine CpG site-specific base sequence, with the number of cloning products having a unmethylated cytosine CpG site-specific base sequence.

Examples of the sixth technique include bisulfite direct sequencing and bisulfite cloning sequencing (see Kristensen L S et al., Clin Chem, 2009, 55, 1471-1483).

The seventh technique is a method based on the following principles. First, a bisulfite treatment is performed on the genomic DNA. Next, the region containing the CpG site is amplified by PCR using the bisulfite-converted nucleotide containing the CpG site as a template. Next, the amplified DNA fragment is treated with a restriction enzyme that recognizes the site having a different sequence depending on whether the CpG site is methylated or not. Then, the DNA methylation level of the CpG site can be calculated by quantitatively analyzing the band intensity of the restriction enzyme fragment derived from the methylated CpG site and the restriction enzyme fragment derived from the unmethylated CpG site, which have been fractionated by electrophoresis.

An example of the seventh technique is COBRA (analysis by the combined use of bisulfite and a restriction enzyme).

The eighth technique is a method using ion exchange chromatography. For example, the eighth technique is a method based on the following principles. First, a bisulfite treatment is performed on the genomic DNA. Then, it is fragmented to obtain DNA fragments containing a CpG site. The regions containing the CpG sites are amplified by PCR using the obtained DNA fragments as a template. Next, the amplified DNA fragments are run through ion exchange chromatography to separate the DNA in which the CpG sites are methylated from the DNA in which the CpG sites are not methylated.

In the eighth technique, the length of the PCR amplification products can be appropriately selected while considering factors such as shortening the PCR amplification time, and shortening the analysis time and preserving the separation performance in the ion exchange chromatography. For example, the length of the PCR amplification products when using a sample DNA with many CpG sites is preferably 1000 bp or less, more preferably 700 bp or less, and further preferably 500 bp or less. On the other hand, the lower limit of the length of the PCR amplification products when using a sample DNA with a few CpG sites is 30 to 40 bp, which is the length of the PCR amplification products when using a primer of around 15 mer which can avoid non-specific hybridization in PCR. On the other hand, it is preferable to design the primer to have a rich content of CpG sites. For example, it is preferable that the cytosine of the CpG site be contained in 2% or more, more preferably 5% or more, with respect to the length of the PCR amplification products.

In the eighth technique, the unmethylated cytosine residues are converted to uracil by bisulfite treatment of genomic DNA and then further converted to thymine by PCR. On the other hand, the methylated cytosine residues remain as cytosine even after a bisulfite treatment and PCR. Due to this difference in base, the fragments containing methylated cytosine (methylated fragments) and the unmethylated fragments are detected as separate peaks with different retention times in ion exchange chromatography. That is, the methylated fragments are detected as peaks having a shorter retention time than the unmethylated fragments. Therefore, it is possible to determine whether the DNA at the CpG site is methylated or not based on the retention time of the peak in ion exchange chromatography. Furthermore, when the DNA run through the ion exchange chromatography contains a plurality of CpG sites, the more CpG sites are methylated, the shorter the retention time of the peak is. Therefore, the DNA methylation level at the CpG site can be calculated based on the retention time of the peak. Alternatively, it is also possible to calculate the abundance and abundance ratio of each of methylated fragment and unmethylated fragment based on the area or height of the peak.

Preferably, whether the DNA of the CpG site is methylated or not, or the DNA methylation level of the CpG site is determined by comparison with a sample (control) having a known DNA methylation level of the CpG site or by using a calibration curve prepared in advance using a sample having a known DNA methylation level. Alternatively, a retention time serving as a reference (also referred to as the reference retention time in this description) for separating the retention time of the peak of a methylated fragment having a highly methylated CpG site from the retention time of the peak of a fragment having a low methylation level using a sample having a known DNA methylation level, is determined in advance. For example, a fragment detected at a retention time earlier than the reference retention time is determined to be highly methylated DNA.

The ion exchange chromatography performed in the eighth technique is preferably an anion exchange chromatography. The packing material of the column is not particularly limited as long as it is made of base material particles having a strong cationic group on the surface, but base material particles having both a strong cationic group and a weak cationic group on the packing material surface, as shown in WO 2012/108516, are preferable. More preferably, the base material particles are base material particles containing coated polymer particles in which a layer of a hydrophilic polymer having a strong cationic group (preferably a quaternary ammonium salt) is copolymerized on the surface of hydrophobic crosslinked polymer particles, and a weak cationic group (preferably a tertiary amino group) introduced on the surface of the coated polymer particle. The column temperature in the chromatographic analysis is preferably 30° C. or more and less than 90° C.

The techniques that can be suitably used as a "technique for detecting the DNA methylation level" in the present invention have been exemplified above, but they are not limited thereto. In the first to eighth techniques, as described above, the genomic DNA prepared from urothelial tissue is further subjected to a bisulfite treatment. Therefore, the genomic DNA used for detecting the DNA methylation level of a CpG site in the method of the present invention is preferably bisulfite-treated genomic DNA derived from a urothelial cell or a tissue containing the same.

In the method of the present invention, the risk of canceration of a tested urothelial tissue, or the risk of urothelial carcinoma of a subject is determined from the detected DNA methylation level of the CpG site. Preferably, it is determined whether the risk of canceration of the tested urothelial tissue is high, or whether the subject has a high risk of urothelial carcinoma. More preferably, it is determined whether the tested urothelial tissue has a high risk of having urothelial carcinoma in the future, or whether the subject has a high risk of developing urothelial carcinoma in the future. A specific index for risk determination can be appropriately set by a person skilled in the art according to the technique for detecting the DNA methylation level An embodiment of the procedure for risk determination will be described below. In a first embodiment, first, for each DNA methylation level detection technique, a receiver operating characteristic (ROC) analysis is performed for each CpG site to obtain the sensitivity (positive rate) and specificity (negative rate), then the DNA methylation level in which the sum of the sensitivity and the specificity is maximum is set as an index (cutoff value).

In the first embodiment, for the CpG sites in which the methylation level is increased by the canceration of the urothelial tissue (for example, the CpG sites of TENM3 shown in Table 1), the DNA methylation level is considered to exceed the diagnostic threshold when the DNA methylation level detected with the method of the present invention is higher than the cutoff value, and the test tissue or subject is classified into the high risk group, but when the detected methylation level is equal to or below the cutoff value, the test tissue or subject is classified as not in the high risk group. On the other hand, for the CpG sites in which the methylation level is reduced by the canceration of the urothelial tissue (for example, the CpG sites of HOXC4, TLR1, CPVL and PRDM16 shown in Table 1), the DNA methylation level is considered to exceed the diagnostic threshold when the DNA methylation level detected with the method of the present invention is lower than the cutoff value, and the test tissue or subject is classified into the high risk group, but when the detected methylation level is equal to or above the cutoff value, the test tissue or subject is classified as not in the high risk group.

In the first embodiment, when the methylation levels of a plurality of CpG sites are detected, the number or ratio of CpG sites in which the DNA methylation level exceeds the diagnostic threshold can be used as an index for risk determination. For example, a test tissue or a subject can be classified into the high risk group when the methylation levels of all the investigated CpG sites exceed the diagnostic threshold. Alternatively, a test tissue or a subject can be classified into the high risk group when the methylation levels of a certain percentage or more of the investigated CpG sites exceed the diagnostic threshold. Alternatively, a test tissue or a subject can be classified into the high risk group when the methylation levels of a certain number or more of the CpG sites exceed the diagnostic threshold. On the other hand, the test tissues or subjects that do not meet these criteria can be classified as not in the high risk group.

In a second embodiment of the procedure for risk determination, the methylation level of a CpG site or the risk of urothelial carcinoma is determined by comparing the retention time of the peak obtained by the ion exchange chromatography analysis (the eighth technique) on the DNA (sample) containing the target CpG site derived from the test tissue or the subject, with the retention time for the DNA containing the unmethylated target CpG site (negative control) or the DNA containing the methylated target CpG site (positive control).

In the second embodiment, for a CpG site in which the methylation level is increased by the canceration of urothelial tissue (for example, the CpG sites of TENM3 shown in Table 1), when a peak with a shorter retention time than that of the negative control is detected from the sample, the sample is considered to be methylated, or the test tissue or subject is classified into the high risk group. Alternatively, when a peak with a retention time similar to that of the positive control is detected from the sample, the sample is considered to be methylated, or the test tissue or subject is classified into the high risk group. On the other hand, for a CpG site in which the methylation level is reduced by the canceration of urothelial tissue (for example, the CpG sites of HOXC4, TLR1, CPVL and PRDM16 shown in Table 1), when a peak with a longer retention time than that of the positive control is detected from the sample, the sample is considered to be unmethylated, or the test tissue or subject is classified into the high risk group. Alternatively, when a peak with a retention time similar to that of the negative control is detected from the sample, the sample is determined to be unmethylated, or the test tissue or subject is classified into the high risk group.

Thus, according to the present invention, the risk of urothelial carcinoma can be determined by a simple technique before histologically clear precancerous lesions such as dysplasia occur. Moreover, according to the present invention, the risk of urothelial carcinoma of a subject can be determined without having to perform a skillful examination such as histological observation. If the patients in the high risk group of developing urothelial carcinoma can be discovered early by the method of the present invention, preventive intervention can be performed to prevent the development of urothelial carcinoma, or early treatment can improve their life prognosis. Alternatively, if the patients who are not at high risk of developing urothelial carcinoma can be screened by the method of the present invention, the number of medical examination visits can be reduced and the QOL can be improved.

Therefore, the present invention also relates to the preventive intervention in subjects classified into the high risk group for urothelial carcinoma according to the method of the present invention. This allows the prevention, early diagnosis, or early treatment of urothelial carcinoma in subjects of the high risk group. Furthermore, the present invention provides a method for treating urothelial carcinoma, which includes treating a subject determined to have urothelial carcinoma by the method of the present invention.

Examples of the means of treatment include surgery and chemotherapy with drugs, radiation, but are not particularly limited thereto.

Furthermore, the present invention provides a primer or a probe for determining the risk of canceration of a urothelial tissue or the risk of urothelial carcinoma of a subject. The primer or probe has a length of at least 12 bases, and hybridizes to at least one CpG site contained in at least one gene selected from the group consisting of five genes (TENM3, HOXC4, TLR1, CPVL and PRDM16) which has been treated with bisulfite. Preferably, the primer or probe hybridizes to at least one CpG site on any one of the fives genes (TENM3, HOXC4, TLR1, CPVL and PRDM16). The examples of the CpG sites of TENM3, HOXC4, TLR1, CPVL and PRDM16 are as shown in Table 1 above.

An example of the primer or probe of the present invention is a primer or probe that hybridizes to at least one CpG site contained in the region set forth in any of SEQ ID NOs: 1 to 5, preferably the region set forth in any of SEQ ID NOs: 1 to 4. Another example of the primer of the present invention is a primer that amplifies the region set forth in any of SEQ ID NOs: 1 to 5, more preferably the region set forth in any of SEQ ID NOs: 1 to 4.

A preferable example of the primer or probe of the present invention is a primer or probe that hybridizes to the regions containing the CpG sites in the bisulfite-treated DNA fragments of the five genes, and that is constructed so as to have a base complementary to methylated cytosine or unmethylated cytosine at the 3'-terminus (for example, a primer or probe that can be used in the above-mentioned first technique).

Another preferable example of the primer or probe of the present invention is a primer (sequencing primer) capable of performing an extension reaction one base at a time from the vicinity of the bases of the CpG sites in the bisulfite-treated DNA fragments of the five genes (for example, a primer or probe that can be used in the above-mentioned third technique). Another preferable example is a probe that hybridizes to the nucleotides containing the CpG sites in the bisulfite-treated DNA fragments of the five genes (for example, a primer or probe that can be used in the above-mentioned fourth technique).

Another preferable example of the primer or probe of the present invention is a primer set capable of specifically amplifying the regions containing the methylated or unmethylated CpG sites in the bisulfite-treated DNA fragments of the five genes (for example, a primer set that can be used for the PCR amplification in the above-mentioned fifth technique or eighth technique).

The length of the primer or probe of the present invention may be at least 12 bases, and is preferably at least 15 bases, more preferably at least 20 bases, further preferably 15 to 40 bases. Moreover, the primer or probe of the present invention may be labeled (for example, fluorescently labeled). In addition, the primer or probe of the present invention is preferably a primer or probe that can be used in any of the first to eighth techniques. Moreover, the primer of the present invention is preferably a PCR primer.

More preferable examples of the primer or probe of the present invention include polynucleotides consisting of the nucleotide sequences set forth in SEQ ID NOs: 6 to 15 and the complementary strands thereof. Further preferable examples include primer sets consisting of a combination of the polynucleotides set forth in SEQ ID NOs: 6 and 7 or the complementary strands thereof, a combination of the polynucleotides set forth in SEQ ID NOs: 8 and 9 or the complementary strands thereof, a combination of the polynucleotides set forth in SEQ ID NOs: 10 and 11 or the complementary strands thereof, a combination of the polynucleotides set forth in SEQ ID NOs: 12 and 13 or the complementary strands thereof, or a combination of the polynucleotides set forth in SEQ ID NOs: 14 and 15 or the complementary strands thereof.

Furthermore, the present invention provides a kit for determining the risk of canceration of a urothelial tissue or the risk of urothelial carcinoma of a subject, which contains the primer or probe of the present invention. Preferably, the kit of the present invention is used for determining the risk of canceration of a urothelial tissue or the risk of urothelial carcinoma of a subject by any of the first to eighth techniques.

The kit of the present invention can contain components other than the primer or probe of the present invention. Examples of such components include reagents necessary for the bisulfite treatment (for example, a sodium bisulfite solution and the like), reagents necessary for the PCR reaction (for example, deoxyribonucleotides, thermostable DNA polymerase and the like), reagents necessary for the Infinium (registered trademark) assay (for example, nucleotides labeled with a fluorescent substance), reagents necessary for MassARRAY (registered trademark) (for example, RNase for performing a base-specific cleavage reaction), reagents necessary for pyrosequencing (for example, ATP sulfurylase for detecting pyrophosphate, adenosine-5'-phosphosulfate, luciferase, luciferin, streptavidin for separating single-stranded DNA, and the like), reagents necessary for the MS-HRM method (for example, intercalators that emit fluorescence when inserted between DNA duplexes, and the like), reagents necessary for the detection of the labels (for example, a substrate or an enzyme), positive control and negative control samples, buffer solutions and the like used for diluting or washing the samples (genomic DNA derived from tissue and the like). Moreover, the kit can also include an instructions leaflet.

EXAMPLES

Hereafter, the present invention is described in detail with examples, but the present invention is not limited to the following examples.
[Patient and Tissue Sample]

Non-cancerous urothelial tissues (N) (n=47) and urothelial carcinoma tissues (T) (n=46) obtained from urothelial carcinoma cases, and normal urothelial tissues (C) (n=26) obtained from non-urothelial carcinoma cases were used as a sample. Tissue samples were obtained from patients who had surgery at the National Cancer Center Hospital. Written informed consent was obtained from all patients. In addition, all the studies in the present examples were carried out with the approval of the Ethics Committee of the National Cancer Center.

The collected tissues were cryopreserved. Genomic DNA was extracted by treating the obtained fresh frozen tissue samples with phenol-chloroform followed by dialysis. 500 ng of the extracted DNA was treated with bisulfite using EZ DNA Methylation-Gold™ kit (manufactured by Zymo Research).

Example 1: Detection of CpG Site Methylation in Cancerous Tissues (Infinium (Registered Trademark) Assay)
The DNA methylation state at the 485,764 CpG sites was analyzed at single-CpG site resolution using Infinium (registered trademark) Human Methylation 450K Bead Chip (manufactured by Illumina). The Infinium (registered trademark) Human Methylation 450K Bead Chip (manufactured by Illumina) is said to cover 99% of RefSeq genes and 96% of CpG islands. More specifically, it is said to include the promoter region, 5' untranslated region, first exon, gene body, and 3' untranslated region as target of analysis, and to cover 99% of reference sequence genes, for the purpose of comprehensively analyzing the DNA methylation state.

A whole genome amplification treatment was performed on the bisulfite-treated DNA using Infinium (registered trademark) assay kit (manufactured by Illumina) (see Bibikova, M., et al., Epigenomics, 2009, 1, 177-200). The amplified DNA fragments were hybridized with the probes on the chip, and then fluorescently labeled bases were incorporated into the hybridized DNA by a single-base extension reaction. As a result, the probe for detecting methylation hybridized with the DNA fragment containing methylated CpG and the probe for detecting unmethylation hybridized with the DNA fragment containing unmethylated CpG were each fluorescently labeled. Next, the fluorescence signal was measured using iScan Reader (manufactured by Illumina) according to the manufacturer's protocol. The obtained data was analyzed using GenomeStudio methylation software (manufactured by Illumina).
(Calculation of DNA Methylation Level)

At each CpG site, the relative ratio of the signal from the probe for detecting methylation to the total of signals from the probe for detecting methylation and the probe for detecting unmethylation was calculated. That is, the methylation level from each CpG site was expressed as a so-called β value (range: 0.00 to 1.00).
(Statistical Analysis)

A Welch t test was performed on the obtained methylation level data, and the CpG sites showing significant abnormal methylation in the (N) sample compared to the (C) sample were identified. Next, the CpG sites in which the DNA methylation level was gradually changed from (C) to (N) to (T) were identified by the Jonckheere-Terpstra trend test. As a result, 2,750 CpG sites were found significant in both tests. Abnormal DNA methylation at these sites was considered to contribute to the canceration of urothelial tissue since it occurred significantly more in non-cancerous tissues (N) of urothelial carcinoma patients than in normal tissues (C), and the frequency thereof further increased in cancerous tissues (T).
(Principal Component Analysis)

A principal component analysis was performed on the DNA methylation level (β value) of the 2,750 CpG sites. As a result, since (C), (N), and (T) showed clearly different distributions (FIG. 1), it was presumed that (N) is a precancerous stage already accompanied by abnormal DNA methylation.

(ROC Analysis)

In order to examine whether (N) can be distinguished from (C) using abnormal DNA methylation as an index, a ROC analysis was performed on the 2,750 CpG sites. A ROC curve based on the sensitivity and specificity was created for the methylation level of each site, and the methylation level at which the sum of the sensitivity and specificity is maximum (when it is closest to the upper left corner of the ROC curve graph) was set as a tentative diagnostic threshold (cutoff value). That is, for the CpG sites in which DNA methylation was increased in (N) compared to (C), the sample was considered to meet the diagnostic threshold (high risk of canceration) when the DNA methylation level of the sample was higher than the cutoff value. Conversely, for the CpG sites in which DNA methylation was reduced in (N) compared to (C), the sample was considered to meet the diagnostic threshold (high risk of canceration) when the DNA methylation level of the sample was lower than the cutoff value. Furthermore, the area under the curve (AUC) of the ROC curve was measured for each site.

Figure 2:
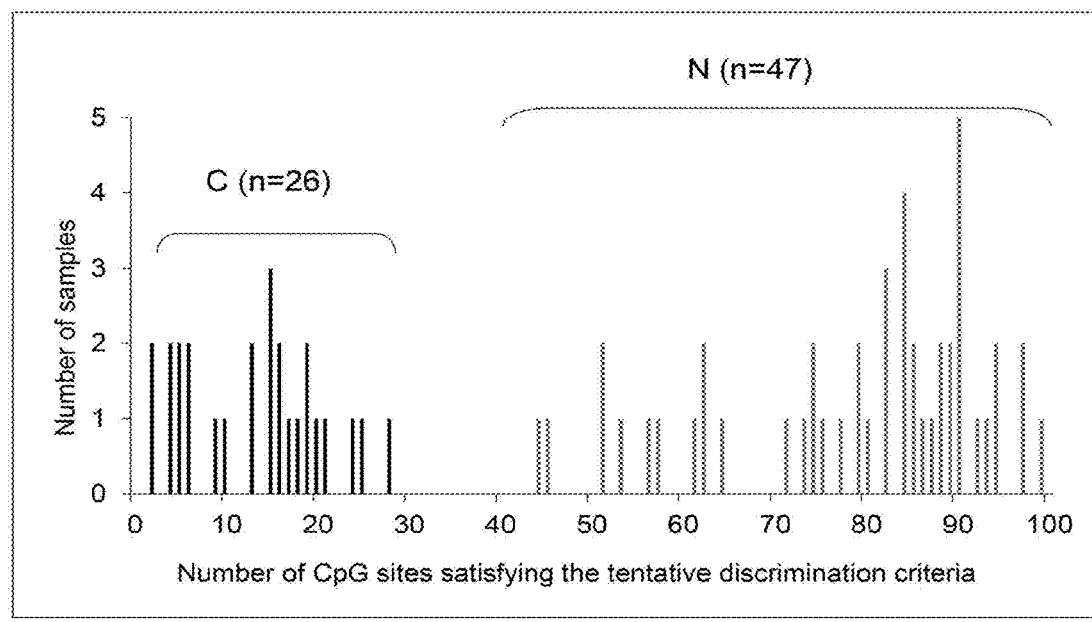
FIG. 2 Histogram of the number of CpG sites satisfying the diagnostic threshold in normal tissues (C) and non-cancerous tissues of patients with urothelial carcinoma (N).

FIG. 2 shows a histogram which sets the number of CpG sites satisfying the diagnostic threshold on the horizontal axis and the number of samples on the vertical axis. The histogram is bimodal where (C) and (N) are clearly separated, and it was confirmed that (C) and (N) show clearly different methylation profiles. Therefore, it was considered possible to distinguish the samples that have developed or are likely to develop urothelial carcinoma from the samples that are unlikely to develop urothelial carcinoma, on the basis of the DNA methylation level of these CpG sites, and to determine the risk of urothelial carcinoma.

Example 2: Evaluation of Urothelial Carcinoma Markers

Five genes (TENM3, HOXC4, TLR1, CPVL and PRDM16) containing the CpG sites having an AUC of the ROC curve created in Example 1 of 0.95 or more were selected, and the DNA methylation level at the CpG sites of these genes was confirmed by MassARRAY (registered trademark) or pyrosequencing.

(MassARRAY (Registered Trademark) Method)

The MassARRAY (registered trademark) method is a method which amplifies bisulfite-treated DNA, transcribes it into RNA, and further cleaves it base-specifically with RNase, then detects the difference in molecular weight between the methylated DNA fragments and unmethylated DNA fragments by a mass spectrometer.

The primers for MassARRAY were designed using EpiDesigner (manufactured by SEQUENOM, primer design software for MassARRAY) for the CpG sites of the TENM3 gene. For each designed primer set, a combination of 3 types of DNA polymerase and conditions with an annealing temperature of about 4 steps was averaged and tried to determine the optimal PCR conditions with good quantitative performance. It was confirmed that the quantitative performance was good under the PCR conditions adopted for all the CpG sites to be analyzed. Since the PCR target sequence in MassARRAY is rather long, about 100 to 500 bp, the DNA methylation level of multiple CpG sites around the target CpG site can be evaluated together. The primer sequences and PCR conditions used in the present analysis are shown in Table 3, and the target sequence is shown in Table 4.

TABLE 3

| Target gene | Target ID (Infinium assay probe ID) | | Primer | SEQ ID NO | PCR conditions |
|---|---|---|---|---|---|
| TENM3 | cg06366833 | Forward | 5'-TTTTAGTGTTTTG GATGATTGTTA-3' | 6 | [95° C., 15 min] → [95° C., 20 s → 54° C., 30 s → 72° C., 60 s] × 45 cycles → [72° C., 3 min] |
| | | Reverse | 5'-ACAAAAACCTCCT TTCAATTAACTTT-3' | 7 | |

TABLE 4

| Target gene | Target sequence | SEQ ID NO |
|---|---|---|
| TENM3 | 5'-GATCGAACAACAAAGACAGAAAAGATCTAT GACGACCACCGTAAATTTCTACTGAGGATCGCC TACGACACGTCTGGGCACCCGACTCTCTGGCTG CCAAGCAGCAAGCTGATGGCCGTCAATGTCACC TATTCATCCACAGGTCAAATTGCCAGCATCCAG CGAGGCACCACTAGCGAGAAAGTAGATTATGAC GGACAGGGGAGGATCGTGTCTCGGGTCTTTGCT GATGGTAAAACATGGAGTTACACATATTTAGAA AAGGTATGCCTGCAAACTAAGCTCAACAATAGG GAAAGGATAATTCACATTTT-3' | 1 |

The bisulfite-treated DNA was amplified by PCR, and then an in vitro transcription reaction was performed. The obtained RNA was specifically cleaved at the uracil site by RNase to produce fragments of different lengths according to the presence or absence of methylation of the genomic DNA of each sample. The obtained RNA fragments were run through MALDI-TOF MS (manufactured by SEQUENOM, MassARRAY (registered trademark) Analyzer 4), which can detect the difference in mass of a single base, to perform a mass spectrometry. The obtained mass spectrometry results were aligned to a reference sequence using an analysis software (EpiTYPER, manufactured by SEQUENOM), and the methylation level was calculated from the mass ratio between the RNA fragments derived from methylated DNA and the RNA fragments derived from unmethylated DNA.

(Pyrosequencing)

Pyrosequencing was performed under the conditions shown in Table 5. The target sequences are shown in Table 6.

TABLE 5

| Target gene | Target ID (Infinium assay probe ID) | | Primer | SEQ ID NO | PCR conditions |
|---|---|---|---|---|---|
| HOXC4 | cg19696083 | Forward | 5'-TGGTAGAGGGGTATAGGGGAATTT-3' | 8 | [95° C., 5 min] → [95° C., 30 s → 56° C., 30 s → 72° C., 30 s] × 50 cycles → [72° C., 5 min] |
| | | Reverse | 5'-CAAACTACAAAATTTCCTCCATTCA-3' | 9 | |
| TLR1 | cg22839308 | Forward | 5'-GGGTTTATAAAATTTTGGGGTTT-3' | 10 | [95° C., 15 min] → [95° C., 30 s → 58° C., 30 s → 72° C., 30 s] × 50 cycles → [72° C., 5 min] |
| | | Reverse | 5'-AAAACAATTTTATCATCCCCACAT-3' | 11 | |
| CPVL | cg14772935 | Forward | 5'-TGTAGGAGTGAGTTTAGGGAAATT-3' | 12 | [95° C., 5 min] → [95° C., 30 s → 60° C., 30 s → 72° C., 30s] × 5 cycles → [95° C., 30 s → 58° C., 30 s → 72° C., 30 s] × 5 cycles → [95° C., 30 s → 56° C., 30 s → 72° C., 30 s] × 40 cycles → [72° C., 5 min] |
| | | Reverse | 5'-AATCCTCACAACAACCCAATAAA-3' | 13 | |
| PRDM16 | cg01448098 | Forward | 5'-GTGTTTAGGGAAAAGTTTATTGGAA-3' | 14 | [95° C., 15 min] → [95° C., 30 s → 54° C., 30 s → 72° C., 30 s] × 50 cycles → [72° C., 5 min] |
| | | Reverse | 5'-ATTTTCCTACCCCCAACATCT-3' | 15 | |

TABLE 6

| Target gene name | Target sequence | SEQ ID NO |
|---|---|---|
| HOXC4 | 5'-TCGTGTACCGCAT-3' | 2 |
| TLR1 | 5'-TCCAGTCAAAACCGGAT-3' | 3 |
| CPVL | 5'-GCAGCCCAGCCAACCCGAC-3' | 4 |
| PRDM16 | 5'-CGTGAGG-3' | 5 |

(Results)

Figure 3:
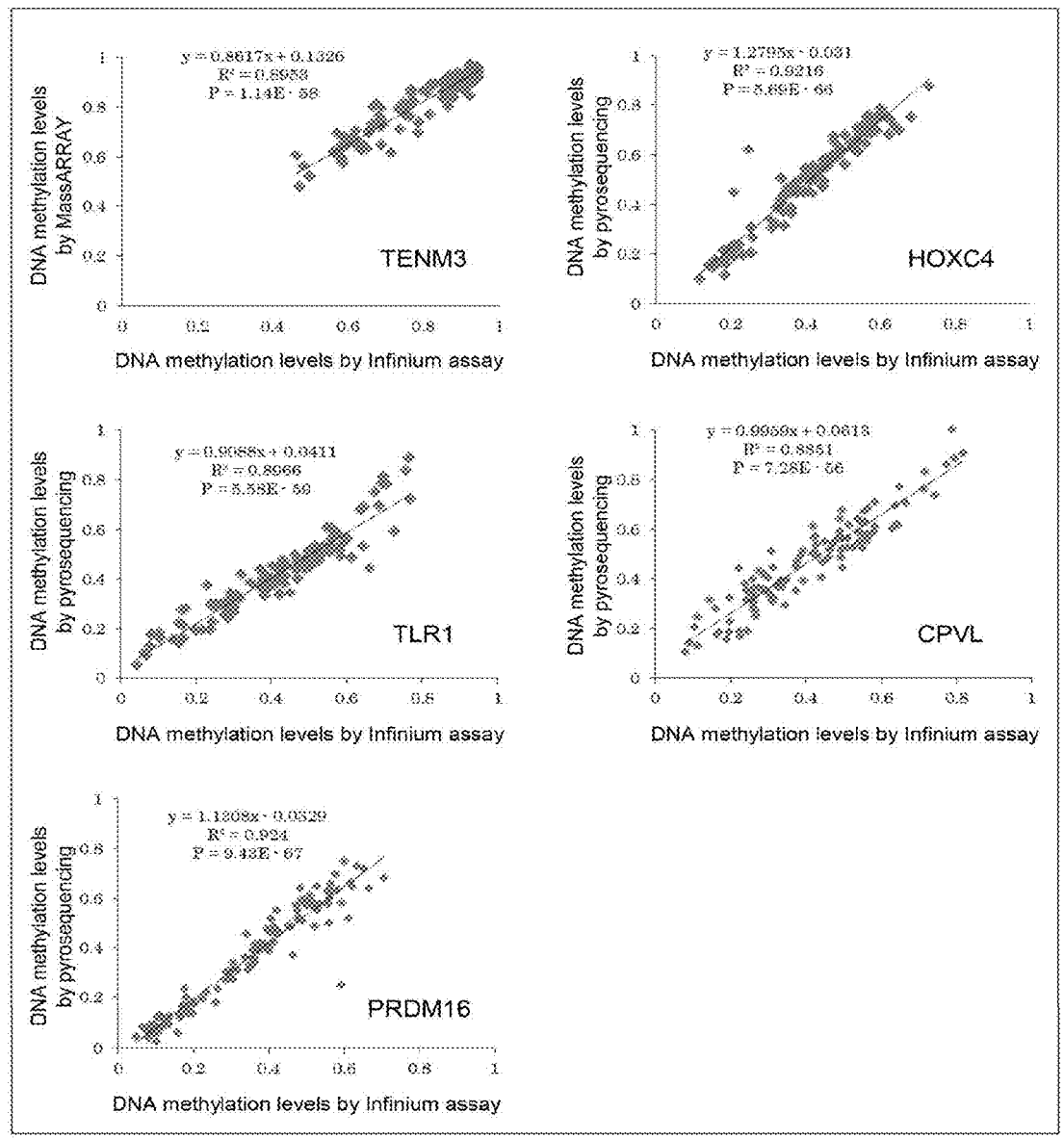
FIG. 3 Correlation of DNA methylation level detection values between the Infinium (registered trademark) assay and pyrosequencing or MassARRAY (registered trademark).

As a result, a strong correlation was found between the analysis results by MassARRAY (registered trademark) or pyrosequencing and the analysis results by Infinium (registered trademark) assay for all of the five genes (FIG. 3). Therefore, it was shown that the CpG sites of these five genes can be used as a marker for determining the risk of urothelial carcinoma.

ROC analysis was performed again for the CpG sites of the five genes using the DNA methylation levels measured by MassARRAY (registered trademark) or pyrosequencing. Since some CpG sites were close to each other, they were analyzed together as one CpG unit. The results are shown in Table 7.

TABLE 7

| | CpG site or unit | | Methylation level | AUC value | Cutoff value | Sensitivity | Specificity |
|---|---|---|---|---|---|---|---|
| Gene | Chromosome number | Position on the chromosome | | | | | |
| TENM3 | 4 | 183710473 | C < N | 0.98 | 0.73 | 0.91 | 0.96 |
| | 4 | 183710455 | C < N | 0.95 | 0.70 | 0.83 | 0.92 |
| | 4 | 183710441 | C < N | 0.90 | 0.64 | 0.83 | 0.88 |
| | 4 | 183710349, 183710344 | C < N | 0.87 | 0.49 | 0.85 | 0.81 |
| | 4 | 183710318, 183710311 | C < N | 0.91 | 0.63 | 0.81 | 0.88 |
| HOXC4 | 12 | 54438419 | C > N | 0.98 | 0.62 | 0.91 | 0.96 |
| | 12 | 54438426 | C > N | 0.95 | 0.84 | 0.87 | 0.88 |
| TLR1 | 4 | 38807259 | C > N | 0.94 | 0.47 | 0.94 | 0.85 |
| CPVL | 7 | 29187019 | C > N | 0.81 | 0.55 | 0.76 | 0.73 |
| PRDM16 | 1 | 3078013 | C > N | 0.90 | 0.52 | 0.81 | 0.92 |

All of the CpG sites or units shown in Table 7 had a large AUC of the ROC curve, and it was shown that they allow to determine the risk of urothelial carcinoma with high sensitivity and specificity even when used alone. Furthermore, it was expected that sensitivity, specificity, and reproducibility could be further improved by combining these CpG sites or units. Table 8 shows examples of combination of two of the CpG sites or units shown in Table 7. The sensitivity and specificity of the risk determination by these combinations were both 96% or more.

TABLE 8

| CpG site or unit | | | | |
|---|---|---|---|---|
| Gene | Chromosome number | Position on the chromosome | Sensitivity | Specificity |
| TENM3 | 4 | 183710473 | 0.98 | 1.00 |
| HOXC4 | 12 | 54438419 | | |
| TENM3 | 4 | 183710473 | 1.00 | 0.96 |
| HOXC4 | 12 | 54438426 | | |
| TENM3 | 4 | 183710473 | 1.00 | 1.00 |
| TLR1 | 4 | 38807259 | | |
| TENM3 | 4 | 183710473 | 0.98 | 0.96 |
| CPVL | 7 | 29187019 | | |
| TENM3 | 4 | 183710455 | 0.98 | 0.96 |
| HOXC4 | 12 | 54438426 | | |
| TENM3 | 4 | 183710349, 183710344 | 0.96 | 1.00 |
| TLR1 | 4 | 38807259 | | |
| TENM3 | 4 | 183710318, 183710311 | 0.98 | 0.96 |
| HOXC4 | 12 | 54438426 | | |
| TENM3 | 4 | 183710318, 183710311 | 0.96 | 1.00 |
| TLR1 | 4 | 38807259 | | |
| HOXC4 | 12 | 54438419 | 1.00 | 0.96 |
| HOXC4 | 12 | 54438426 | | |
| HOXC4 | 12 | 54438419 | 0.96 | 1.00 |
| TLR1 | 4 | 38807259 | | |
| HOXC4 | 12 | 54438426 | 0.98 | 0.96 |
| TLR1 | 4 | 38807259 | | |
| HOXC4 | 12 | 54438426 | 0.98 | 0.96 |
| CPVL | 7 | 29187019 | | |
| PRDM16 | 1 | 3078013 | 0.96 | 1.00 |
| TLR1 | 4 | 38807259 | | |
| PRDM16 | 1 | 3078013 | 1.00 | 1.00 |
| TENM3 | 4 | 183710473 | | |
| PRDM16 | 1 | 3078013 | 0.96 | 1.00 |
| TENM3 | 4 | 183710349, 183710344 | | |
| PRDM16 | 1 | 3078013 | 0.98 | 1.00 |
| TENM3 | 4 | 183710318, 183710311 | | |
| PRDM16 | 1 | 3078013 | 0.98 | 1.00 |
| HOXC4 | 12 | 54438419 | | |
| PRDM16 | 1 | 3078013 | 0.96 | 1.00 |
| HOXC4 | 12 | 54438426 | | |

The invention claimed is:

1. A method for determining a risk of urothelial carcinoma in a subject, comprising:
   treating genomic DNA obtained from a urothelial cell or a tissue containing the urothelial cell obtained from the subject with bisulfite, wherein the genomic DNA comprises a CpG site of TENM3 and the
   CpG site of the TENM3 comprises at least one CpG site in SEQ NO:1;
   providing a primer or probe comprising the sequence of SEQ ID NO:6 or SEQ ID NO:7;
   hybridizing the primer or probe to the bisulfite treated DNA;
   detecting an increased DNA methylation level at the CpG site of TENM3 in the bisulfite treated genomic DNA; and
   determining an increased risk of urothelial carcinoma in the subject with an increased methylation level.

2. The method of claim 1, wherein the detecting of the DNA methylation level is performed using a pyrosequencing method, mass spectrometry, a bead array method, or ion exchange chromatography.

3. The method of claim 1, wherein the CpG site of the TENM3 is located in at least one position of chromosome 4 selected from the group consisting of position 183,710,473, position 183,710,455, position 183,710,441, position 183,710,349, position 183,710,344, position 183,710,318, and position 183,710,311, all based on NCBI database Genome Build 37.

4. The method according to claim 1,
   wherein the genomic DNA further comprises a CpG site of HOXC4,
   wherein the CpG site of the HOXC4 is at least one CpG site in SEQ ID NO:2,
   and the method further comprises:
   providing a primer or probe, each of which have a length of at least 12 bases to hybridize with the CpG site of HOXC4 in the genomic DNA treated with bisulfite;
   detecting a reduced DNA methylation level at the CpG site of HOXC4 in the bisulfite treated genomic DNA, and
   determining an increased risk of urothelial carcinoma in the subject with an increased DNA methylation levels of the CpG sites of TENM3 and a reduced DNA methylation level of the CpG sites of HOXC4.

5. The method according to claim 1,
   wherein the genomic DNA further comprises a CpG site of TLR1,
   wherein the CpG site of the TLR1 is at least one CpG site in SEQ ID NO:3,
   and the method further comprises:
   providing a primer or probe, each of which have a length of at least 12 bases to hybridize with the CpG site of TLR1 in the genomic DNA treated with bisulfite;
   detecting a reduced DNA methylation level at the CpG site of TLR1 in the bisulfite treated genomic DNA, and
   determining an increased risk of urothelial carcinoma in the subject with an increased DNA methylation levels of the CpG sites of TENM3 and a reduced DNA methylation level of the CpG site of TLR1.

6. The method according to claim 1,
   wherein the genomic DNA further comprises a CpG site of CPVL,
   wherein the CpG site of the CPVL is at least one CpG site in SEQ ID NO:4,
   and the method further comprises:
   providing a primer or probe, each of which have a length of at least 12 bases to hybridize with the CpG site of OWL, in the genomic DNA treated with bisulfite;
   detecting a reduced DNA methylation level at the CpG site of CPVL in the bisulfite treated genomic DNA, and
   determining an increased risk of urothelial carcinoma in the subject with an increased DNA methylation levels of the CpG sites of TENM3 and a reduced DNA methylation level of the CpG site of CPVL.

7. The method according to claim 1,
   wherein the genomic DNA further comprises a CpG site of PRDM16,
   wherein the CpG site of the PRDM16 is at least one CpG site in SEQ ID NO:5,
   and the method further comprises:
   providing a primer or probe, each of which have a length of at least 12 bases to hybridize with the CpG site of PRDM16 in the genomic DNA treated with bisulfite;
   detecting a reduced DNA methylation level at the CpG site of PRDM16 in the bisulfite treated genomic DNA, and
   determining an increased risk of urothelial carcinoma in the subject with an increased DNA methylation levels of the CpG sites of TENM3 and a reduced DNA methylation level of the CpG site of PRDM16.

* * * * *

UNITED STATES PATENT AND TRADEMARK OFFICE
CERTIFICATE OF CORRECTION

PATENT NO. : 11,840,738 B2
APPLICATION NO. : 16/970583
DATED : December 12, 2023
INVENTOR(S) : Yae Kanai et al.

It is certified that error appears in the above-identified patent and that said Letters Patent is hereby corrected as shown below:

In the Claims

Column 32, Claim 6, Line 24, "OWL, in the genomic DNA treated with bisulfite;" should read -- CPVL, in the genomic DNA treated with bisulfite; --.

Signed and Sealed this
Ninth Day of April, 2024

Katherine Kelly Vidal
*Director of the United States Patent and Trademark Office*

```
                         SEQUENCE LISTING

<160> NUMBER OF SEQ ID NOS: 15

<210> SEQ ID NO 1
<211> LENGTH: 314
<212> TYPE: DNA
<213> ORGANISM: Homo sapiens
<220> FEATURE:
<223> OTHER INFORMATION: TENM3

<400> SEQUENCE: 1
gatcgaacaa caaagacaga aaagatctat gacgaccacc gtaaatttct actgaggatc      60
gcctacgaca cgtctgggca cccgactctc tggctgccaa gcagcaagct gatggccgtc     120
aatgtcacct attcatccac aggtcaaatt gccagcatcc agcgaggcac cactagcgag     180
aaagtagatt atgacggaca ggggaggatc gtgtctcggg tctttgctga tggtaaaaca     240
tggagttaca catatttaga aaaggtatgc ctgcaaacta agctcaacaa tagggaaagg     300
ataattcaca tttt                                                       314

<210> SEQ ID NO 2
<211> LENGTH: 13
<212> TYPE: DNA
<213> ORGANISM: Homo sapiens
<220> FEATURE:
<223> OTHER INFORMATION: HOXC4

<400> SEQUENCE: 2
tcgtgtaccg cat                                                         13

<210> SEQ ID NO 3
<211> LENGTH: 17
<212> TYPE: DNA
```

```
<213> ORGANISM: Homo sapiens
<220> FEATURE:
<223> OTHER INFORMATION: TLR1

<400> SEQUENCE: 3
tccagtcaaa accggat                                                        17

<210> SEQ ID NO 4
<211> LENGTH: 19
<212> TYPE: DNA
<213> ORGANISM: Homo sapiens
<220> FEATURE:
<223> OTHER INFORMATION: CPVL

<400> SEQUENCE: 4
gcagcccagc caacccgac                                                      19

<210> SEQ ID NO 5
<211> LENGTH: 7
<212> TYPE: DNA
<213> ORGANISM: Homo sapiens
<220> FEATURE:
<223> OTHER INFORMATION: PRDM16

<400> SEQUENCE: 5 cgtgagg                                                                    7

<210> SEQ ID NO 6
<211> LENGTH: 25
<212> TYPE: DNA
<213> ORGANISM: Artificial
<220> FEATURE:
<223> OTHER INFORMATION: Primer for TENM3

<400> SEQUENCE: 6
ttttagtgtt ttggatgatt gttga                                               25

<210> SEQ ID NO 7
<211> LENGTH: 26
<212> TYPE: DNA
<213> ORGANISM: Artificial
<220> FEATURE:
<223> OTHER INFORMATION: Primer for TENM3

<400> SEQUENCE: 7
acaaaaacct cctttcaatt aactttt                                             26

<210> SEQ ID NO 8
<211> LENGTH: 24
<212> TYPE: DNA
<213> ORGANISM: Artificial
<220> FEATURE:
<223> OTHER INFORMATION: Primer for HOXC4

<400> SEQUENCE: 8
tggtagaggg gtataggga attt                                                 24

<210> SEQ ID NO 9
<211> LENGTH: 25
<212> TYPE: DNA
<213> ORGANISM: Artificial
<220> FEATURE:
<223> OTHER INFORMATION: Primer for HOXC4

<400> SEQUENCE: 9
caaactacaa aatttcctcc attca                                               25
```

```
<210> SEQ ID NO 10
<211> LENGTH: 24
<212> TYPE: DNA
<213> ORGANISM: Artificial
<220> FEATURE:
<223> OTHER INFORMATION: Primer for TLR1

<400> SEQUENCE: 10
gggtttataa aaattttggg gttt                                          24

<210> SEQ ID NO 11
<211> LENGTH: 24
<212> TYPE: DNA
<213> ORGANISM: Artificial
<220> FEATURE:
<223> OTHER INFORMATION: Primer for TLR1

<400> SEQUENCE: 11
aaaacaattt tatcatcccc acat                                          24

<210> SEQ ID NO 12
<211> LENGTH: 24
<212> TYPE: DNA
<213> ORGANISM: Artificial
<220> FEATURE:
<223> OTHER INFORMATION: Primer for CPVL

<400> SEQUENCE: 12
tgtaggagtg agtttaggga aatt                                          24

<210> SEQ ID NO 13
<211> LENGTH: 23
<212> TYPE: DNA
<213> ORGANISM: Artificial
<220> FEATURE:
<223> OTHER INFORMATION: Primer for CPVL

<400> SEQUENCE: 13
aatcctcaca acaacccaat aaa                                           23

<210> SEQ ID NO 14
<211> LENGTH: 25
<212> TYPE: DNA
<213> ORGANISM: Artificial
<220> FEATURE:
<223> OTHER INFORMATION: Primer for PRDM16

<400> SEQUENCE: 14
gtgtttaggg aaaagtttat tggaa                                         25

<210> SEQ ID NO 15
<211> LENGTH: 21
<212> TYPE: DNA
<213> ORGANISM: Artificial
<220> FEATURE:
<223> OTHER INFORMATION: Primer for PRDM16

<400> SEQUENCE: 15
attttcctac ccccaacatc t                                             21
```